United States Patent
Berner

(10) Patent No.: US 12,156,779 B2
(45) Date of Patent: *Dec. 3, 2024

(54) ABUTMENT

(71) Applicant: STRAUMANN HOLDING AG, Basel (CH)

(72) Inventor: Simon Berner, Suhr (CH)

(73) Assignee: STRAUMANN HOLDING AG, Basel (CH)

( * ) Notice: Subject to any disclaimer, the term of this patent is extended or adjusted under 35 U.S.C. 154(b) by 627 days.

This patent is subject to a terminal disclaimer.

(21) Appl. No.: 17/348,472

(22) Filed: Jun. 15, 2021

(65) Prior Publication Data

US 2021/0307880 A1    Oct. 7, 2021

Related U.S. Application Data

(63) Continuation of application No. 14/896,569, filed as application No. PCT/EP2014/001549 on Jun. 6, 2014, now abandoned.

(30) Foreign Application Priority Data

Jun. 7, 2013  (EP) .................................... 13002955

(51) Int. Cl.
| | | |
|---|---|---|
| *C23C 22/06* | (2006.01) | |
| *A61C 8/00* | (2006.01) | |
| *A61L 27/50* | (2006.01) | |
| *C23C 22/77* | (2006.01) | |
| *C23C 22/78* | (2006.01) | |
| *C25D 3/54* | (2006.01) | |
| *C25D 5/34* | (2006.01) | |
| *B82Y 30/00* | (2011.01) | |

(52) U.S. Cl.
CPC ............ *A61C 8/0015* (2013.01); *A61C 8/005* (2013.01); *A61L 27/50* (2013.01); *C23C 22/06* (2013.01); *C23C 22/77* (2013.01); *C23C 22/78* (2013.01); *C25D 3/54* (2013.01); *C25D 5/34* (2013.01); *A61L 2400/12* (2013.01); *A61L 2430/12* (2013.01); *B82Y 30/00* (2013.01)

(58) Field of Classification Search
None
See application file for complete search history.

(56) References Cited

U.S. PATENT DOCUMENTS

| | | | |
|---|---|---|---|
| 7,655,586 B1 | 2/2010 | Brodkin et al. | |
| 7,972,648 B2 | 7/2011 | Berckmans, III et al. | |
| 8,512,741 B2 | 8/2013 | Tan et al. | |
| 9,108,295 B2 | 8/2015 | Hansson | |
| 9,642,680 B2 * | 5/2017 | Berner .................... | C22C 14/00 |
| 9,931,184 B2 | 4/2018 | Hall | |
| 2002/0031749 A1 | 3/2002 | Morgan | |
| 2002/0182567 A1 | 12/2002 | Hurson et al. | |
| 2003/0059742 A1 | 3/2003 | Webster et al. | |
| 2003/0170378 A1 | 9/2003 | Wen et al. | |
| 2004/0054422 A1 | 3/2004 | Descouts et al. | |
| 2004/0152034 A1 | 8/2004 | Cummings et al. | |
| 2005/0031663 A1 | 2/2005 | Larsson et al. | |
| 2006/0154206 A1 | 7/2006 | Petersson et al. | |
| 2006/0204738 A1 | 9/2006 | Dubrow et al. | |
| 2006/0229715 A1 | 10/2006 | Istephanous et al. | |
| 2007/0110890 A1 | 5/2007 | Berckmans et al. | |
| 2007/0275350 A1 | 11/2007 | Hall | |
| 2008/0044795 A1 | 2/2008 | Hall | |
| 2008/0220394 A1 | 9/2008 | Berckmans et al. | |
| 2008/0261178 A1 | 10/2008 | Homann et al. | |
| 2009/0035722 A1 | 2/2009 | Balasundaram et al. | |
| 2009/0164027 A1 | 6/2009 | Zipprich | |
| 2009/0191507 A1 | 7/2009 | Charlton et al. | |
| 2009/0220561 A1 | 9/2009 | Jin et al. | |
| 2010/0173264 A1 | 7/2010 | Fredriksson et al. | |

(Continued)

FOREIGN PATENT DOCUMENTS

| | | |
|---|---|---|
| EP | 2 161 000 A1 | 3/2010 |
| EP | 2314251 A1 | 4/2011 |

(Continued)

OTHER PUBLICATIONS

Videm, K. et al., "Hydride formation on titanium surfaces by cathodic polarization," Applied Surface Science, 2008, pp. 3011-3015, vol. 255.

Mendonça, G. et al., "Advancing dental implant surface technology-From micron- to nanotopography," Biomaterials, 2008, pp. 3822-3835, vol. 29.

Lord, M. et al., "Influence of nanoscale surface topography on protein adsorption and cellular response," Nano Today, 2010, pp. 66-78, vol. 5.

(Continued)

*Primary Examiner* — Shamim Ahmed
*Assistant Examiner* — Bradford M Gates
(74) *Attorney, Agent, or Firm* — Oliff PLC

(57) ABSTRACT

The present invention relates to an abutment of a dental implant system for connecting a dental implant and a suprastructure, said abutment comprising an abutment basic body extending from an apical end to a coronal end arranged opposite to the apical end. The abutment basic body comprises a dental implant connecting portion facing the apical end and adapted to fit with a corresponding abutment connecting portion of the dental implant and/or an intermediate part to be directly or indirectly connected with the dental implant. It further comprises a support portion facing the coronal end and designed such to allow the suprastructure to be mounted directly or indirectly. According to the invention, the abutment further comprises nanostructures formed on at least a portion of the outer surface of the abutment basic body, said nanostructures extending in at least two dimensions to 200 nm at most.

20 Claims, No Drawings

(56) References Cited

U.S. PATENT DOCUMENTS

| | | |
|---|---|---|
| 2010/0255447 A1 | 10/2010 | Biris et al. |
| 2010/0303722 A1 | 12/2010 | Jin et al. |
| 2011/0033661 A1 | 2/2011 | Oawa |
| 2011/0125263 A1 | 5/2011 | Webster et al. |
| 2011/0151026 A1 | 6/2011 | Hansson et al. |
| 2011/0171600 A1 | 7/2011 | Yang et al. |
| 2011/0233169 A1 | 9/2011 | Mayfield et al. |
| 2011/0306016 A1 | 12/2011 | Hansson |
| 2012/0010599 A1 | 1/2012 | Jin et al. |
| 2012/0288699 A1 | 11/2012 | Ahlberg et al. |
| 2013/0045360 A1 | 2/2013 | Ibacache et al. |
| 2013/0189646 A1 | 7/2013 | Hochman et al. |
| 2013/0323678 A1 | 12/2013 | Towse et al. |
| 2014/0186799 A1 | 7/2014 | Pan et al. |
| 2014/0342316 A1 | 11/2014 | Berner et al. |
| 2018/0008213 A1 | 1/2018 | Rubbert |

FOREIGN PATENT DOCUMENTS

| | | |
|---|---|---|
| JP | H11-43799 A | 2/1999 |
| WO | 2013/056844 A1 | 4/2013 |
| WO | 2013180889 A2 | 12/2013 |

OTHER PUBLICATIONS

Mustafa, K. et al., "The influence of surface topography of ceramic abutments on the attachment and proliferation of human oral fibroblasts," Biomaterials, 2005, pp. 373-381, vol. 26.

Yamano, S. et al., "The Influence of Different Implant Materials on Human Gingival Fibroblast Morphology, Proliferation, and Gene Expression," The International Journal of Oral & Maxillofacial Implants, 2011, pp. 1247-1255, vol. 26, No. 6.

Feb. 18, 2015 International Search Report issued in International Patent Application No. PCT/EP2014/001549.

Dec. 8, 2015 International Preliminary Report on Patentability issued in International Patent Application No. PCT/EP2014/001549.

Nov. 21, 2016 Office Action Issued in U.S. Appl. No. 14/896,569.
Jul. 25, 2017 Office Action Issued in U.S. Appl. No. 14/896,569.
Feb. 6, 2018 Office Action Issued in U.S. Appl. No. 14/896,569.
May 10, 2019 Office Action issued in U.S. Appl. No. 14/896,569.
Dec. 31, 2019 Office Action Issued in U.S. Appl. No. 14/896,569.
Aug. 6, 2020 Office Action Issued in U.S. Appl. No. 14/896,569.
Mar. 15, 2021 Office Action Issued in U.S. Appl. No. 14/896,569.
Feb. 11, 2021 Notice of Allowance issued in European Patent Application No. 14729219.7.

\* cited by examiner

ABUTMENT

This is a Continuation of Application Ser. No. 14,896,569 filed Dec. 7, 2015, which in turn is a national stage of PCT/EP2014/001549 filed Jun. 6, 2014, which claims the benefit of EP 13002955.6 filed Jun. 7, 2013. The disclosure of the prior applications is hereby incorporated by reference herein in its entirety.

The present invention relates to an abutment of a dental implant system for connecting a dental implant and a suprastructure as well as to a process for providing sites of improved protein adherence on an abutment basic body.

Dental implants are well known in the art. Generally, they comprise an anchoring part intended to be anchored in a patient's jaw bone and a head part intended to form the basis on which a suprastructure, such as a bridge or crown, is mounted. The mounting of the suprastructure is thereby often performed by using an intermediate, i.e. a so-called □abutment□ (also referred to as □secondary part□), as it is the case in a □two-part implant system□ or □multi-part implant system□.

Apart from being biocompatible and having sufficient mechanical strength, it is required that the implant provides good osteointegration.

The term □osteointegration□ designates the direct structural and functional connection between living bone and the surface of the implant. A good osteointegration means that the implant, after reaching a primary stability by screwing it into the bone, safely ossifies within a healing time so that a permanent bond between implant and bone is obtained.

In the past, much effort has been made in order to improve the osteointegrative properties of implants.

Besides the importance of the implant's osteointegrative properties, there is on-growing evidence that also a good interaction between the implant system and the surrounding supracrestal connective tissue (in the following referred to as the □soft tissue□) is crucial for a successful implantation. This is supported by the view that the soft tissue plays a fundamental role in establishing an effective seal between the oral environment and the endosseous part of a dental implant and, thus, also a barrier for bacteria to adhere on the soft tissue contact surface and the bone tissue contact surface of the implant system.

Indeed, the presence of bacteria on the implant system's surface may lead to an inflammation of the peri-implant mucosa, and, if left untreated, the inflammation spreads apically and results in bone resorption.

As a consequence of the theory that rough surfaces accumulate and retain more plaque than smooth surfaces (see Oral Implantology, Thieme Verlag, 1996, page 438), nowadays, at least the part of the implant system's surface, which comes into contact with the soft tissue, is typically machined.

As mentioned above, the soft tissue contact surface of the implant system would ideally not only provide a surface showing a low tendency for bacteria to adhere, but also allow a relatively strong and fast interaction between the soft tissue and the implant to be established (also referred to as □soft tissue integration□), in order to quickly provide an effective seal between the oral environment and the endosseous part.

This applies not only to the dental implant itself, but also to the abutment of a respective dental implant system.

Aiming at an improved soft tissue integration of the implant system, EP-A-2161000 suggests an abutment comprising a soft tissue contact surface that is at least partially hydroxylated. In this context, improved soft tissue integration is explained by the loose connective tissue to become organized and replaced be newly formed collagen fibers.

Irrespective of the beneficial effects achieved by the technology described in EP-A-2161000, there is an on-going need for further, simple solutions for improving soft tissue integration of the abutment, and ultimately the dental implant system.

The object of the present invention is thus to provide an abutment the outer surface of which establishes a good soft tissue i.e. integration, a relatively strong interaction between abutment and soft tissue in a relatively timely manner, and which at the same time shows a low tendency for bacteria to adhere.

This problem is solved by the subject matter of claim 1. Preferred embodiments of the invention are subject of the dependent claims.

According to claim 1, the present invention relates to a abutment comprising an abutment basic body extending from an apical end to a coronal end arranged opposite to the apical end, the abutment comprising a dental implant connecting portion facing the apical end and adapted to fit with a corresponding abutment connecting portion of the dental implant and/or an intermediate part to be directly or indirectly connected with the dental implant.

The abutment further comprises a support portion facing the coronal end designed such to allow the suprastructure to be mounted directly or indirectly, i.e. using at least one intermediate, as it is the case in multi-part dental implant systems.

According to the invention, the abutment comprises nanostructures formed on the outer surface of the abutment basic body, said nanostructures extending in at least two dimensions to 200 nm at most.

Preferably, the nanostructures are formed on the outer surface of a soft tissue contact region of the abutment basic body, said region being arranged between the dental implant connecting portion and the support portion of the abutment basic body. The outer surface of the soft tissue contact region is in the following also referred to as □soft tissue contact surface□.

The nanostructures form retention sites, allowing for an improved initial adherence of proteins of the cells of the surrounding soft tissue. Without wanting to be bound by the transmembrane theory, proteins, specifically integrins, can directly or indirectly, i.e. by mediation of other proteins, adhere to the nanostructures and, thus, establish an anchorage of the cells to the abutment's soft tissue contact surface. In this complex mechanism, laminins, which is linked with the extracellular domain of the integrins, can also play an important role, as well as plasma proteins, such as albumin, fibrinogen and fibronectin.

Ultimately, the nanostructures forming retention sites allow for an optimal soft tissue interaction of the abutment and, consequently, an effective seal between the dental implant system's endosseous part and the oral environment to be achieved.

According to a particularly preferred embodiment, the outer surface of the abutment basic body on which the nanostructures are formed is smooth, e.g. machined or polished.

In other words, the surface topography is smooth when regarded in macroscopic and microscopic scale, but nevertheless provides a nanoscopic structure due to the presence of the nanostructures. These nanostructures are small enough not to interfere with the low plaque forming tendency of the soft tissue contact surface, but big enough to allow proteins of the surrounding soft tissue cells to adhere.

As a result, the soft tissue contact surface's tendency for adherence of bacteria is low, while at the same time protein adherence of the surrounding soft tissue cells can take place.

Alternatively to the outer surface of the abutment basic body being smooth, it can also be minimally rough, i.e. having a roughness as e.g. obtainable by acid etching.

The term "dental implant" as used in the context of the present invention relates to the primary part of a dental implant system, i.e. the part that is actually implanted in the bone, whereas the term "abutment" relates to the "secondary part" of the dental implant system. The term "suprastructure" relates to the prosthetic element of the dental restoration, and in particular relates to a crown or bridge.

In that the outer surface of the abutment basic body on which the nanostructures are formed, in particular the soft tissue contact surface, is preferably smooth, it is in clear distinction from the bone tissue contact surface of the dental implant, which typically comprises a macroscopic topography, achieved e.g. by sand-blasting and/or machining, as well as a microscopic topography, achieved e.g. by acid etching.

It is understood that the present invention encompasses abutments in which nanostructures are formed on the soft tissue contact surface only, as well as embodiments in which they are formed on the surface of additional regions than the soft tissue contact region, and embodiments in which they are formed on the whole surface of the abutment basic body.

According to a further preferred embodiment, the nanostructures are at least predominantly in crystalline phase. More preferably, the nanostructures are in an at least approximately purely crystalline phase.

The nanostructures can have different shapes including a needle-like shape, a leaf-like shape, a flower-like shape, a sphere-like shape or a nodule-like shape.

In the context of the present invention, the term "needle-like shape" encompasses any shape having a length to diameter ratio of more than 1:1. Thereby, the diameter is to be understood as the expansion of the nanostructure in a direction perpendicular to the longitudinal direction.

Preferably, the nanostructures have an average length-to-diameter ratio of more than 1 to 1, more preferably of at least 1.5 to 1, most particularly ranging from 1.5 to 1 to 4 to 1.

As mentioned, the nanostructures according to the present invention preferably extend in at least two dimensions to 200 nm at most. More specifically, the nanostructures preferably have an average diameter of about 10 nm to 150 nm and an average length of about 5 nm to 500 nm.

It has further been found that by the presence of nanostructures, a relatively high hydrophilicity of the abutment's surface can be achieved, which can further contribute to a good soft tissue interaction. According to a preferred embodiment, at least a part of the surface of the abutment, thus, has a hydrophilicity defined by a contact angle of less than 90°, more preferably less than 30°, most preferably less than 10°, when contacted with water.

It is further preferred that the abutment basic body is made of titanium or a titanium alloy. A respective basic body allows nanostructures to be formed on its surface in a relatively simple and reproducible manner, as will be shown below.

In view of its use in the field of implantology, and in particular oral implantology, any suitable grade of titanium or titanium alloy known to the skilled person can be used, including titanium of grade 2 to grade 4.

When using a titanium alloy, this is preferably a titanium zirconium (TiZr) alloy, typically comprising Zr in an amount of 13 to 17%. Alternatively, a titanium aluminium vanadium alloy, specifically Ti-6Al-4V (TAV), or a titanium aluminium niobium alloy, specifically Ti-6Al-7Nb (TAN), can be used as a titanium alloy suitable for the purpose of the present invention.

With regard to the use of titanium or a titanium alloy for the abutment basic body, it is further preferred that the nanostructures comprise titanium hydride and/or titanium oxide.

In case the nanostructures comprise titanium hydride, they typically comprise $TiH_2$, whereas in case the nanostructures comprise titanium oxide, they typically comprise $TiO_2$.

According to a further aspect, the present invention also relates to a process for providing sites of improved protein adherence on an abutment basic body, as described above.

According to this process, the nanostructures are grown on the outer surface of the abutment basic body by treating the outer surface of the abutment basic body with an aqueous solution.

The feature that the nanostructures are grown means that they are not formed by a mechanical removing process or by subjecting the surface of the body to other mechanical structuring processes. Rather, the formation of the nanostructures occurs gradually in that they "build up" over time by treating the outer surface of the abutment basic body with the aqueous solution.

The term "aqueous solution" as used in the context of the present invention encompasses both pure water as well as a solution in which the solvent is water.

A particularly good formation/growing of nanostructures has been observed for embodiments in which the aqueous solution is an acidic solution comprising at least one component selected from the group consisting of hydrogen fluoride, nitric acid, hydrochloric acid, sulphuric acid, tartaric acid, oxalic acid, citric acid and acetic acid, and/or mixtures thereof.

As mentioned above, the abutment basic body is typically made of titanium or a titanium alloy.

According to a well-controllable and thus preferred process, the growing of the nanostructures is performed by cathodic polarization (also referred to as "cathodic hydridation"), in which the abutment basic body forms the cathode. A detailed description of this process will be given by way of the examples below.

In this regard, it is particularly preferred that before performing cathodic polarization, at least a portion of the outer surface of the abutment basic body is pickled with a pickling solution in order to at least partially remove a titanium oxide layer present the outer surface. A pickling solution comprising at least one component selected from the group consisting of nitric acid, hydrofluoric acid, ammonium fluoride, hydrochloric acid and sulphuric acid, and/or mixtures thereof, particularly a mixture of nitric acid and hydrofluoric acid, is thereby preferably used.

With regard to the cathodic polarization, this is preferably performed in a buffer having a pH in the range from 0 to 6. The temperature is preferably set in a range from 5 to 95° C., preferably from 10 to 75° C., more preferably from 15 to 50° C., most preferably at about room temperature.

Additionally or alternatively to the above described process using cathodic polarization, the nanostructures can be grown on the outer surface of the abutment basic body by storing the outer surface of the abutment basic body in the aqueous solution.

The storing is typically carried out by using a 0.9% NaCl solution, more specifically having a pH of 2 to 7, preferably 3 to 6. Likewise, any other suitable aqueous solution can be used including pure water.

According to a particularly preferred embodiment, the storing is carried out for at least one month, more preferably at least two months, most preferably at least four months. The storage time depends on the surface topography of the outer surface of the abutment basic body. For a machined surface, the storage times required for the growing of the nanostructures has been found to be longer than for a rough surface. However, also for a machined surface, nanostructures are detected after two months of storing.

With regard to the storing, it is further preferred that this is performed at an elevated temperature, i.e. a temperature above room temperature, since nanostructure formation has been shown to be particularly pronounced at these temperatures.

A temperature in a range of about 50° C. to 250° C., more particularly about 100° C. to 180° C., and most preferably about 120° C. to 150° C. has been shown to be particularly preferred, since the storing time required for the growing of nanostructures can be shortened substantially. A storing over months is, thus, not required when performing a (hydro-) thermal treatment at the temperatures specified above.

It is understood that the process of the present invention encompasses embodiments in which only the soft tissue contact region is subjected to the treatment with the aqueous solution, as embodiments well as in which additional regions and embodiments in which the whole surface are/is subjected to this treatment.

As mentioned, embodiments in which the outer surface of the abutment basic body on which the nanostructures are formed is smooth, preferably machined or polished. Depending on the actual aim to be achieved, alternative embodiments can be preferred, in which the outer surface of the abutment basic body on which the nanostructures are formed is rough. This is due to the finding that nanostructure formation has been shown to be favoured on a roughened surface.

The present invention is further exemplified by way of the following examples:

EXAMPLES

Treatment of the Samples

Titanium samples were grinded and polished and were then washed with NaOH at 40% (w/v) and $HNO_3$ at 40% (w/v) in an ultrasonic bath to remove contaminants, then washed with deionized water to reach a neutral pH and stored at room temperature in 70 vol.-% ethanol.

After the polishing and cleaning steps, some of the samples were treated (□pickled□) for one minute in a solution containing 15 wt.-% $HNO_3$ and 5 wt.-% HF (solution C1) at room temperature (samples p1). Alternatively, samples were treated in a solution C1 diluted twice with deionized water (samples p2), diluted five times with deionized water (samples p5) and diluted ten times with deionized water (samples p10).

Immediately after the pickling treatment, the samples were washed by dipping in a beaker containing deionized water for 10 seconds, then mounted on a sample holder forming a cathode for cathodic polarization (or cathodic hydridation).

For the cathodic hydridation, current densities at 5, 10 and 15 mA/cm2 were used. The hydration was performed at room temperature and the duration of the hydridation was set to 0.5, 2 and 5 hours. As electrolyte, tartaric acid at 1 M of concentration, pH 1.9, was used.

Nanoscale Analysis of the Samples

Following the hydridation step, a nanoscale analysis of each of the modified surfaces was performed using a Field Emission Scanning Electron Microscope (FE-SEM; Quanta 200F, FEI, The Netherlands).

Thereby, nanostructures, in the particular case nanonodules, with a diameter well below 200 nm were detected as white □spots□. These nanostructures form retention sites for improved protein adherence of the surrounding soft tissue.

The invention claimed is:

1. A process for providing sites of improved protein adherence on an abutment basic body of an abutment for a dental implant system for connecting a dental implant and a suprastructure, the process comprising:
   growing nanostructures that extend in at least two dimensions to 200 nm at most on an outer surface of the abutment basic body by storing the abutment basic body in an aqueous solution for at least one month.

2. The process according to claim 1, wherein the abutment basic body is made of titanium or a titanium alloy.

3. The process according to claim 1, wherein the aqueous solution is an acidic solution comprising at least one component selected from the group consisting of hydrogen fluoride, nitric acid, hydrochloric acid, sulphuric acid, tartaric acid, oxalic acid, citric acid, acetic acid, and mixtures thereof.

4. The process according to claim 1, wherein the storing is performed for at least two months.

5. The process according to claim 1, wherein the storing is performed for at least four months.

6. The process according to claim 1, wherein the storing is performed above room temperature.

7. The process according to claim 1, wherein the storing is performed at a temperature in a range of 50° C. to 250° C.

8. The process according to claim 1, wherein the storing is performed at a temperature in a range of 100° C. to 180° C.

9. The process according to claim 1, wherein the storing is performed at a temperature in a range of about 120° C. to 150° C.

10. The process according to claim 1, wherein the abutment basic body extends from an apical end to a coronal end arranged opposite to the apical end and comprises:
    a dental implant connecting portion at the apical end and adapted to fit with a corresponding abutment connecting portion of the dental implant and/or an intermediate part to be directly or indirectly connected with the dental implant; and
    a support portion at the coronal end and designed to allow the suprastructure to be mounted directly or indirectly thereon.

11. The process according to claim 10, wherein:
    the abutment basic body further includes a soft tissue contact region arranged between the dental implant connecting portion and the support portion and configured to contact and interact with soft tissue; and
    the nanostructures are formed on an outer surface of the soft tissue contact region.

12. The process according to claim 1, wherein the outer surface of the abutment basic body on which the nanostructures are grown is machined or polished.

13. The process according to claim 1, wherein the nanostructures comprise titanium hydride and/or titanium oxide.

14. The process according to claim 1, wherein the nanostructures are at least predominantly in a crystalline phase.

15. The process according to claim 1, wherein the nanostructures have an average length-to-diameter ratio of more than 1:1.

16. The process according to claim 15, wherein the average length-to-diameter ratio of the nanostructures is in a range from 1.5:1 to 4:1.

17. The process according to claim 1, wherein the nanostructures have an average diameter in a range of about 10 nm to 150 nm and an average length in a range of about 5 nm to 500 nm.

18. The process according to claim 1, wherein at least a part of a surface of the abutment has a hydrophilicity defined by a contact angle of less than 90° when contacted with water.

19. The process according to claim 1, wherein at least a part of a surface of the abutment has a hydrophilicity defined by a contact angle of less than 30° when contacted with water.

20. The process according to claim 1, wherein the outer surface of the abutment basic body on which the nanostructures are grown is microscopically and macroscopically smooth.

\* \* \* \* \*